United States Patent [19]
Allen et al.

[11] Patent Number: 6,142,950
[45] Date of Patent: Nov. 7, 2000

[54] NON-TETHERED APNEA SCREENING DEVICE

[75] Inventors: Richard P. Allen, Arnold; David T. Krausman, Kingsville, both of Md.

[73] Assignee: Individual Monitoring Systems, Inc., Baltimore, Md.

[21] Appl. No.: 09/208,899

[22] Filed: Dec. 10, 1998

[51] Int. Cl.[7] .................................................. A61B 5/08
[52] U.S. Cl. ............................................................ 600/529
[58] Field of Search .......................... 600/310, 483–484, 600/519, 529, 532–533, 538, 543

[56] References Cited

U.S. PATENT DOCUMENTS

| | | | |
|---|---|---|---|
| 4,895,162 | 1/1990 | Dolliver | 128/721 |
| 4,999,772 | 3/1991 | Bowman et al. | 364/413.05 |
| 5,107,855 | 4/1992 | Harrington | 128/721 |
| 5,191,893 | 3/1993 | Reiten | 128/721 |
| 5,275,159 | 1/1994 | Griebel | 128/633 |
| 5,295,490 | 3/1994 | Dodakian | 128/721 |
| 5,605,151 | 2/1997 | Lynn | 128/633 |
| 5,611,349 | 3/1997 | Halleck et al. | 128/721 |
| 5,615,688 | 4/1997 | O'Dwyer | 128/716 |
| 5,704,345 | 1/1998 | Berthon-Jones | 128/204.23 |
| 5,765,563 | 6/1998 | Vander Schaaf | 128/725 |
| 5,797,852 | 8/1998 | Karakasoglu et al. | 600/529 |

*Primary Examiner*—Samuel G. Gilbert
*Assistant Examiner*—Ryan Carter
*Attorney, Agent, or Firm*—Larry J. Guffey

[57] ABSTRACT

The present invention provides a method and a device for evaluating a fully ambulatory subject for sleep apnea. In a preferred embodiment, this method is seen to comprise the steps of (1) locating on the subject's upper lip an airflow sensor that is connected with a miniature, recording unit which has: (a) signal conditioning and filtering circuitry to yield required levels of airflow sensor signal fidelity, (b) a programmable controller having an analog to digital converter, an integrated recorder, a data display means, and firmware that analyzes the airflow sensor signal, (c) a mini jack connected to the recorder that connects with a smart cable to control data flow between the recorder and an external computer (2) using this unit to sample at prescribed time intervals the sensor data which effectively quantifies the temporal variation of the subject's inspiration and expiration airflow, (3) time stamping and storing this sampled data in the integrated recorder, (4) using the firmware to identify, count and cause the display of the number of apnea events identified as occurring per a specified period of time, and (5) using an external computer with application software to analyze and display the data for further evaluation of sleep apnea events.

20 Claims, 9 Drawing Sheets

ND INVENTION

BACKGROUND OF THE INVENTION

1. Field of the Invention

The present invention generally relates to physiological monitoring devices. More particularly, this invention relates to a screening device and method for monitoring the occurrence of sleep disorder breathing events (e.g., decreases of upper respiratory airflow lasting more than ten seconds) in a fully ambulatory subject.

2. Description of the Related Art

The diagnosis of a patient's sleep disorders often involves the analysis of the patient's sleep-related events, such as sleep disordered breathing. Such breathing disorders may involve pauses in breathing. These are defined by the American Sleep Disorder Association and the American Sleep Apnea Association as being sleep "apnea" if the pause lasts ten or more seconds, with these being further identified as: (1) Central Apnea—cessation of airflow (upper airway—oral and nasal) and respiratory effort (amplitude of chest movement during breathing); (2) Obstructive Apnea—cessation of airflow with continuation of respiratory effort; and (3) Hypopnea—decrease in airflow from baseline (typically one-third to one-half or more) with continuation of normal or decreased levels of respiratory effort. These events lead to decreased blood oxygenation and thus to disruption of sleep.

Such events are often analyzed by the use of polysomnography (PSG), the monitoring and recording over an extended period of time of the temporal variations in the amplitude of the patient's sleep-impacted, physiological parameters, including: heart rate, eye blink activity, upper respiratory airflow, thorax and abdomen respiration efforts, the blood's oxygen saturation level, electroencephalograms (EEG; electrical activity of the brain), electro-oculogram (EOG; electrical activity related to movement of the eyes), and electromyograms (EMG; electrical activity of a muscle).

Figure 1A:
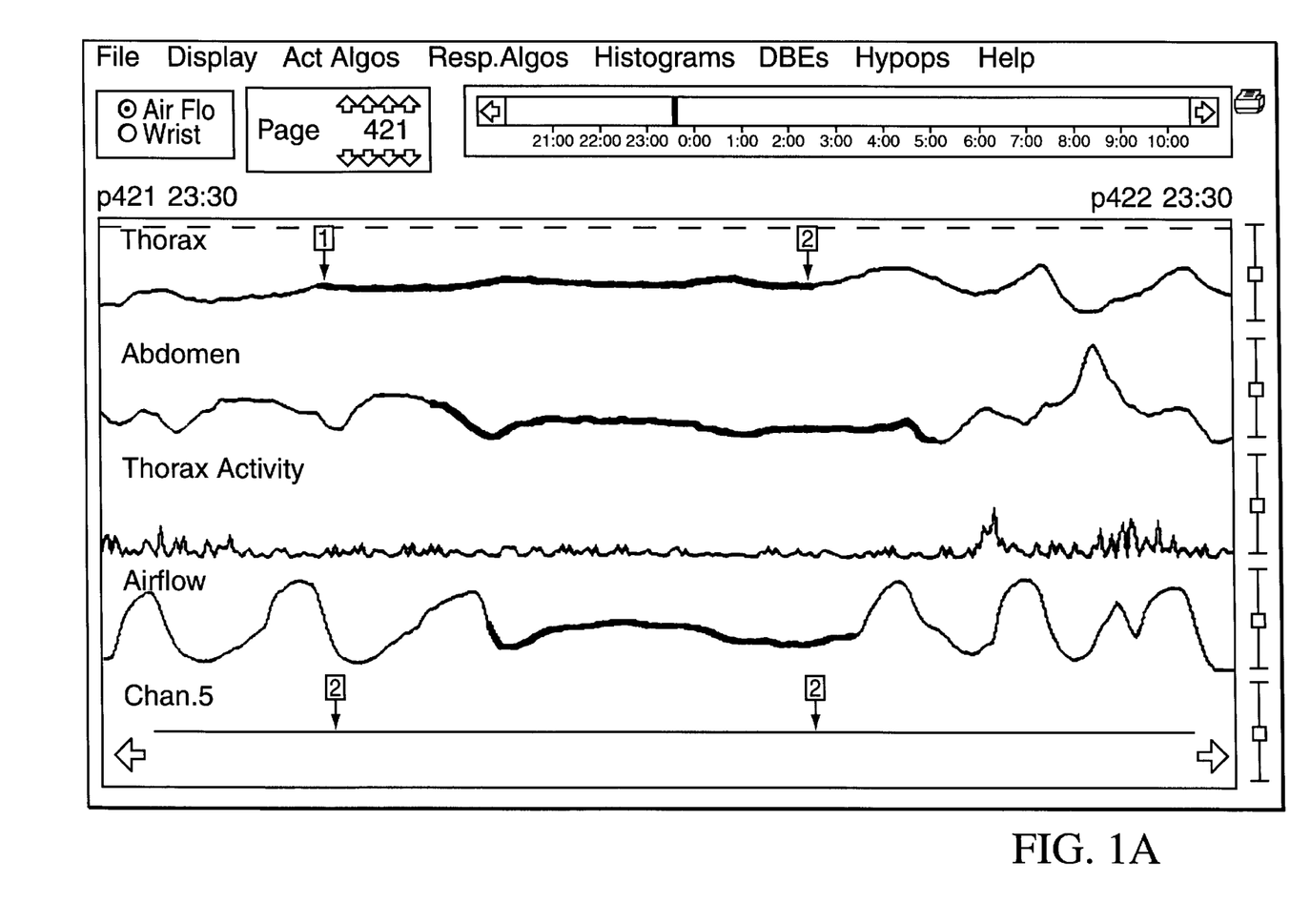
Figure 1B:
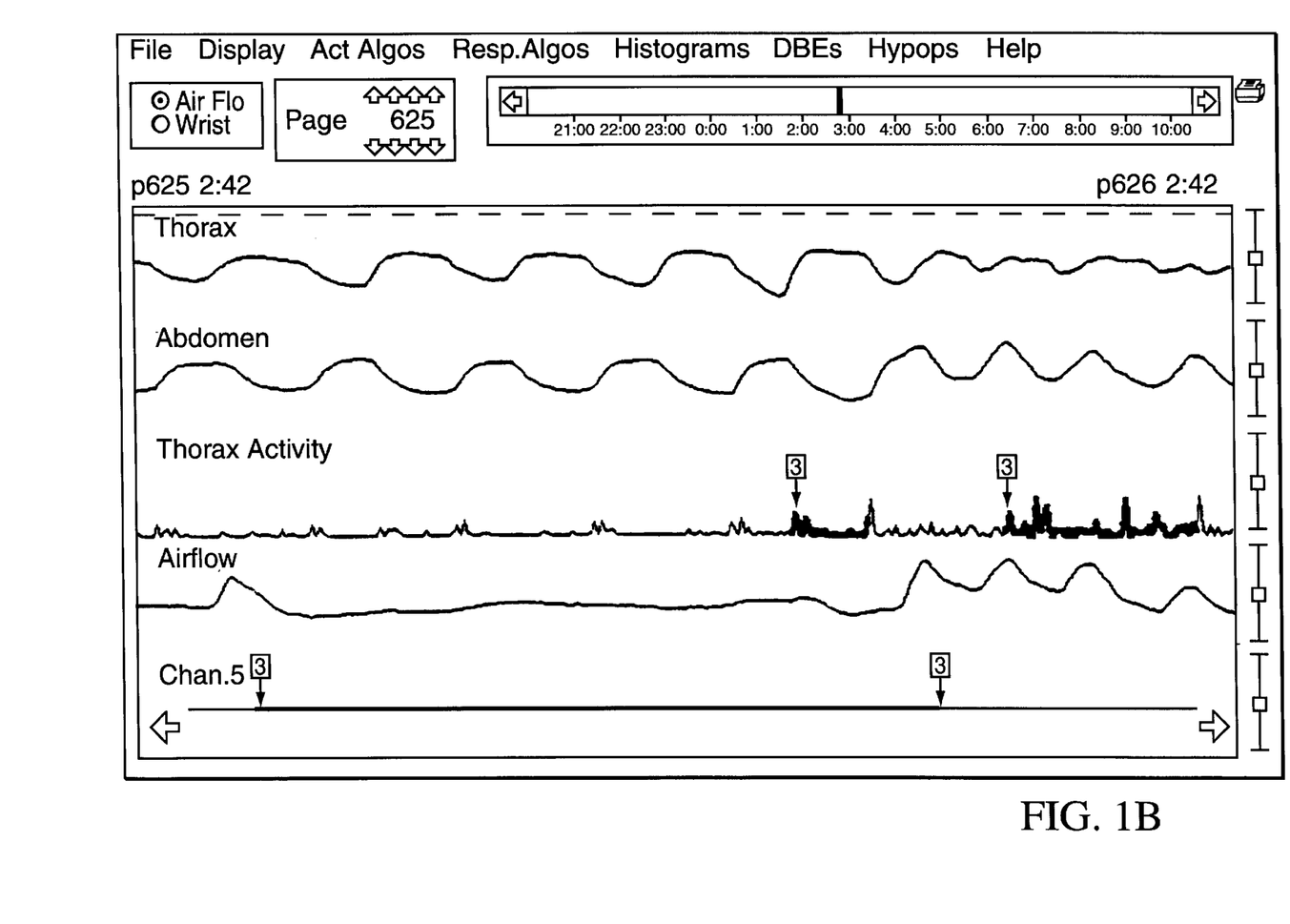
Figure 1C:
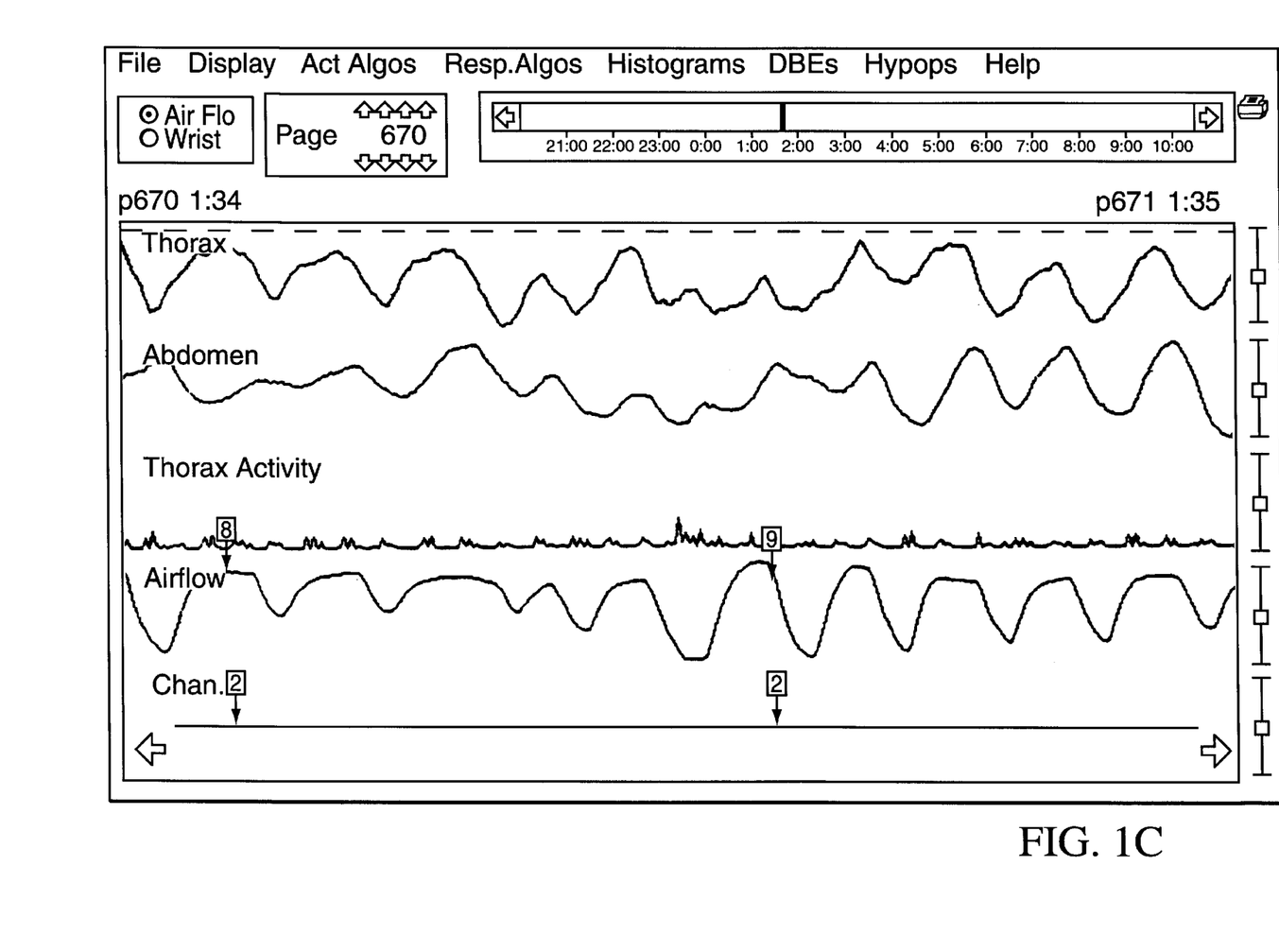

FIG. 1 displays portions of PSG computer tracings for three distinct, thirty-second intervals. Each of these printouts, showing the outputs from four of the system's sensors (i.e., upper respiratory airflow, thorax and abdomen respiration effort, and thorax activity)., illustrates temporal variations which are representative of the sleep-related apnea events defined above: FIG. 1A—Central Apnea, where the airflow sensor shows a marked cessation of airflow which lasted ten or more seconds, with cessation of respiratory effort indicated by the thorax and abdomen sensors; FIG. 1B—Obstructive Apnea, where the airflow signal ceases for ten or more seconds, but the thorax and abdomen sensors show no reduction in respiratory efforts; and FIG. 1C—Hypopnea, where airflow decreases by one-third or more for ten or more seconds and respiratory efforts are also significantly decreased.

PSG monitoring activities are expensive as they are typically conducted in clinical settings by trained PSG technicians who utilize expensive monitoring equipment having multiple sensors that are tethered to a centralized recording system and power supply.

More recently, a number of portable recording systems for diagnosing sleep disorders have been marketed. These systems range from multi-channel, PSG-style systems to much simpler units that monitor only one or more of the possible physiological parameters of interest. However, these multi-channel, portable systems remain technically complex, expensive and usually require trained PSG technicians to supervise their use.

All of the current, portable sleep testing systems share common, less-than-desirable features: (1) their use is expensive, since the equipment itself is expensive and a technician usually must be involved for its set-up and disconnection, plus the data collected must be subjectively analyzed by highly trained, sleep professionals, and (2) the PSG systems are bedside portable, but their use requires patients to be outfitted with an array of tethered electrode wires and sensors for connection to bulky body monitors or table-top consoles; thus, their size and weight does not allow the patient to be ambulatory, which can be essential for diagnosing patients' problems such as excessive sleepiness, or in the evaluation of treatment efficiency and compliance.

Less expensive alternatives, with capabilities for unattended, ambulatory use, are needed for assisting with the diagnosis of patients suffering from sleep disorders. For example, an inexpensive preliminary screening device, that provides information as to which patients might benefit the most from complete PSG testing, could contribute greatly by effectively expanding the audience to whom PSG testing would be available.

Recognizing the need for an improved apparatus or method for diagnosing of the sleep disorders of a fully ambulatory subject, it is therefore a general object of the present invention to provide a novel method and ambulatory, non-tethered apnea screening device to meet such needs.

SUMMARY OF THE INVENTION

The present invention is generally directed to satisfying the needs set forth above and the problems identified with prior portable, sleep testing systems. The problems associated with the expense of PSG testing thereby limiting the number of patients who are assessed for sleep disorders and the non-ambulatory nature of such testing are resolved by the present invention.

In accordance with one preferred embodiment of the present invention, the foregoing need can be satisfied by providing a method for evaluating a fully ambulatory subject for sleep apnea, comprising the steps of (1) locating, on or near the subject's upper lip and in proximity to the nostrils and mouth, a multi-element airflow sensor assembly that measures both nasal and oral airflow, with these airflow being physically and electrically combined, this sensor assembly being connected with a miniature, selfcontained, recording unit which has: (a) signal conditioning and filtering circuitry to yield required levels of airflow sensor signal fidelity, (b) a programmable controller having an analog to digital converter, an integrated recorder, a data display means, and firmware that analyzes the airflow sensor signal, (2) using this unit to sample at prescribed time intervals the sensor data which effectively quantifies the temporal variation of the subject's combined oral and nasal airflow, (3) time stamping and storing this sampled data in the integrated recorder, (4) using the firmware to identify, count and cause the display of the number of apnea events identified as occurring per a specified period of time.

In another preferred embodiment, the present invention is seen to take the form of a non-tethered, apnea screening device. It comprises: (1) an upper airways sensing assembly located so as to measure the subject's inspiration and expiration activity, (2) a miniature, self-contained, recording unit integrated with the sensor, this recording unit having: (a) signal conditioning and filtering circuitry to yield required levels of signal fidelity, (b) a programmable controller connected to the sensor and circuitry, (c) an analog to digital converter, (d) an integrated recorder, and (e) a data display means connected to the controller, wherein the programmable controller has firmware that analyzes the upper airways inspiration and expiration signal to identify, count, and display in the display means the number of occurrences of specifically defined apnea events.

In another preferred embodiment, the non-tethered, apnea screening device further comprises: (3) a control switch connected to the controller which allows the display means to recall and display the number of apnea events counted for each of the consecutive, specified periods of time that comprise the total period over which the upper ventilating measurements were recorded, and to reset the controller to begin s again to count apnea events when the switch remains depressed beyond a specified period of time, (4) a mini jack connected to the controller, and (5) a smart cable that connects with the mini jack to control data flow between the recorder and an external computer, wherein the external computer has application software which is used to analyze and display the temporal variations in the upper airways data for the purpose of evaluating the ambulatory subject for sleep apnea.

Other objects and advantages of this invention will become readily apparent as the invention is better understood by reference to the accompanying drawings and the detailed description that follows.

BRIEF DESCRIPTION OF THE DRAWINGS

FIG. 1 displays partial-PSG computer tracings for three distinct, thirty-second intervals, each of which illustrate a different form of a "sleep apnea" event: 1A—Central Apnea, 1B—Obstructive Apnea, and 1C—Hypopnea.

DESCRIPTION OF THE PREFERRED EMBODIMENT

Referring again to FIG. 1 and the previously given definitions for a central apnea, obstructive apnea and hypopnea, it can be noted that knowledge of a patient's respiration effort (amplitude of the physical movement of the chest) is not required to identify an "apnea" event—such knowledge is only needed to distinguish between the various types of apnea events (e.g., central or obstructive apnea). This suggests the possibility of developing an apnea detection apparatus and an apnea detection method by monitoring only a patient's upper respiratory airflow.

Validation of such an apnea detection method was accomplished through an SBIR research contract (#N43-NS-5-2328) from the National Institute of Neurological Disorder and Stroke. Seven patients with symptoms of sleep disordered breathing were tested in a clinical setting. Each subject in seven separate, all-night sleep studies was fitted with four non-tethered, portable recorders including the present invention containing an oral/nasal airflow sensor placed on or near the upper lip.

Two other recorders configured as chest-belt units were placed about the chest for separately monitoring the respiration effort of the thorax and the respiration effort of the abdomen. These units used piezoelectric sensors that measured the expansion and contraction of the chest belts. A forth chest-belt monitor recorded thorax movement activity using a piezoelectric sensor. Additionally, each patient was fitted with a standard array of sensors and electrodes to provide a PSG recording on a polygraph recorder.

After the night's sleep, data from the non-tethered recorders was downloaded to an external computer, compared to the PSG polygraph tracings and scored by a Diplomat of the American Board of Sleep Disorders Medicine. The Diplomat reviewed both the displayed computer records and the polygraph records. The sleep apnea events, determined by computer display and analysis of the monitor's data, showed excellent correlations with those from the visually scored polysomnogram (PSG). The data shown in FIG. 1 is from these sleep studies and was recorded using the non-tethered, portable recorders.

The above described method of monitoring respiratory ventilation via upper airflow presents a less complex alternative to standard PSG testing and has been shown to provide sufficient information for the detection and counting of apnea events. In effect, this study's data demonstrated that using the upper respiratory ventilation function alone is a useful method for screening apnea and a means for assessing treatment effects or changes in the patient's breathing disorder during sleep.

Figure 2:
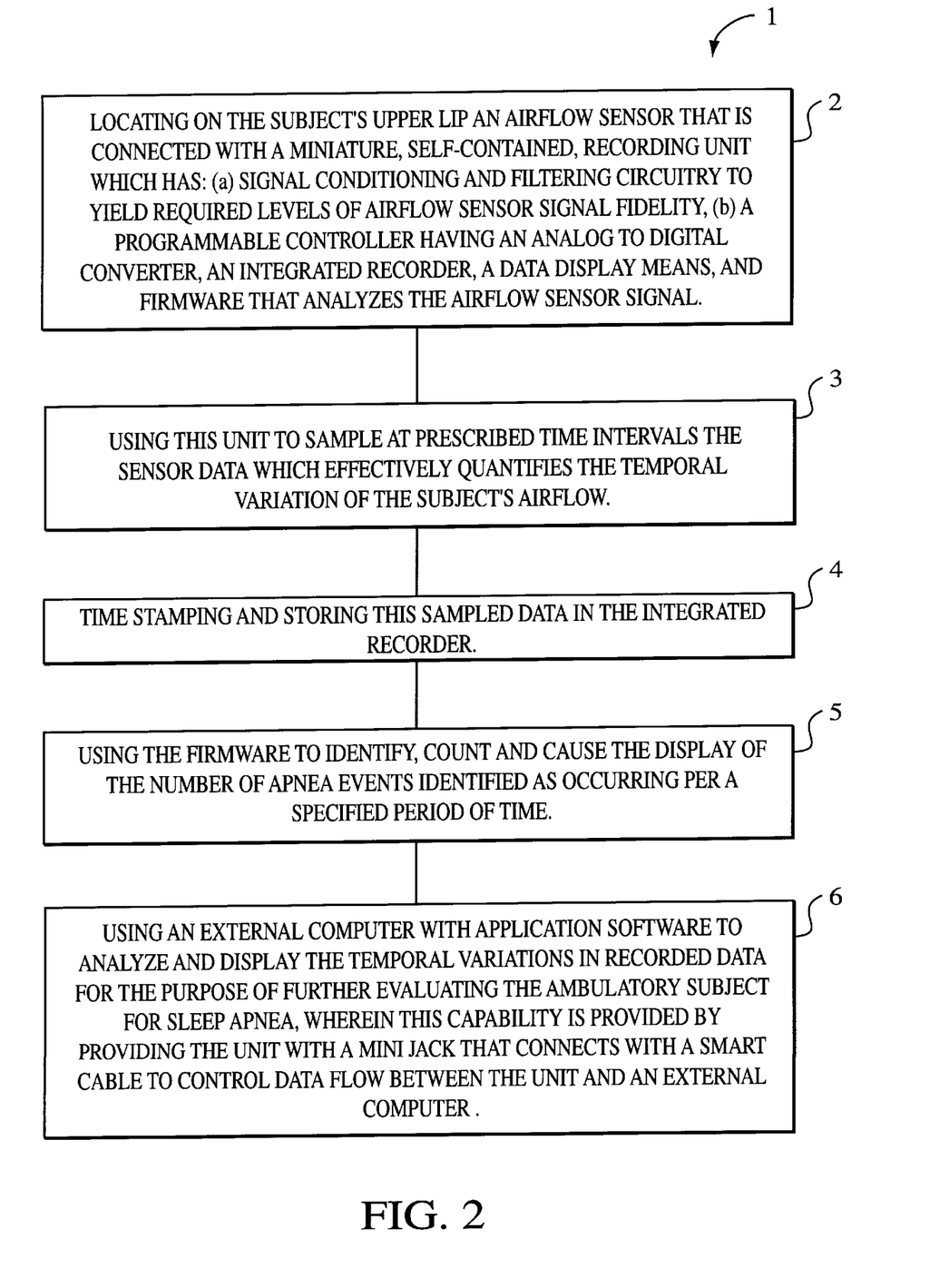
FIG. 2 is a schematic flow diagram which depicts a method in accordance with a preferred embodiment of the present invention.

Referring now to the drawings wherein are shown preferred embodiments and wherein like reference numerals designate like elements throughout, there is shown in FIG. 2 a schematic flow diagram which depicts a method in accordance with a preferred embodiment of the present invention for evaluating a fully ambulatory subject for sleep apnea.

In this embodiment the method 1 is seen to comprise the steps of: (1) locating 2 on the subject's upper lip an airflow sensor that is connected with a miniature, recording unit, this unit having signal conditioning and filtering circuitry to yield required levels of airflow sensor signal fidelity, a programmable controller with an analog to digital converter, an integrated recorder and a data display means, with the programmable controller having firmware that allows the unit to identify, count and record the number of occurrences of sleep apnea events, (2) using 3 the unit to sample at prescribed time intervals sensor data that quantifies the temporal variation of the subject's airflow, (3) time stamping and storing 4 the sampled data in unit's recorder, (4) using 5a the firmware to identify, count and record in the unit's recorder the number of occurrences of sleep apnea events, and (5) using 5b the display means to visually communicate the number of apnea events identified by the firmware as occurring per a specified period of time, typically an hour.

The versatility of the display means may be enhanced by providing the controller with a control switch that allows the display means to recall and display the number of apnea events counted for each of the consecutive, specified periods of time that comprise the total period over which the airflow measurements were recorded, and to reset the controller to begin again to count apnea events when the switch remains depressed beyond a specified period of time, typically about five seconds.

In another embodiment of the present invention, the above method further comprises the step of using 6 an external computer with application software to analyze and display the temporal variations in recorded data for the purpose of further evaluating the ambulatory subject for sleep apnea. This capability is provided by providing the unit with a mini jack that connects with a smart cable to control data flow between the unit and an external computer.

Figure 3:
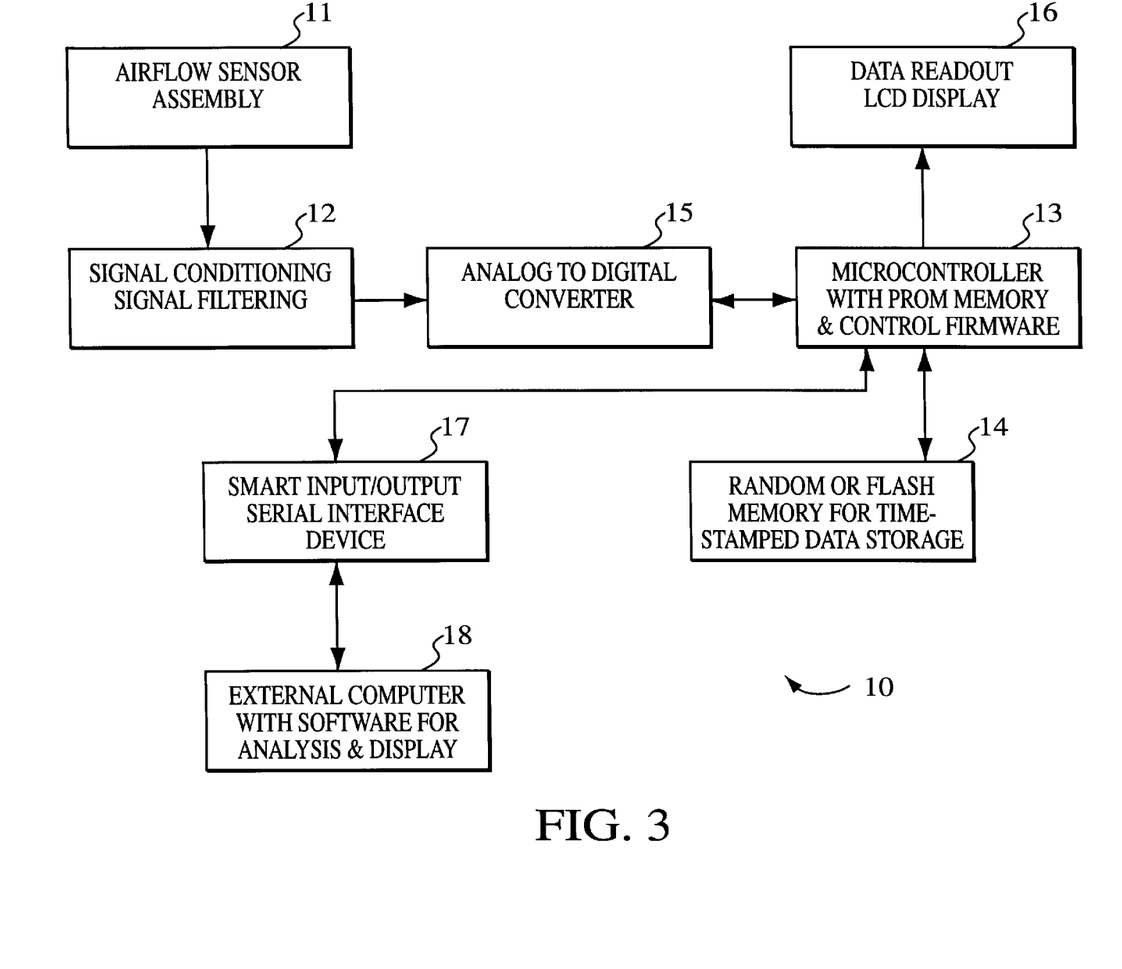
FIG. 3 is a schematic flow diagram of an embodiment of the present invention.
Figure 4:
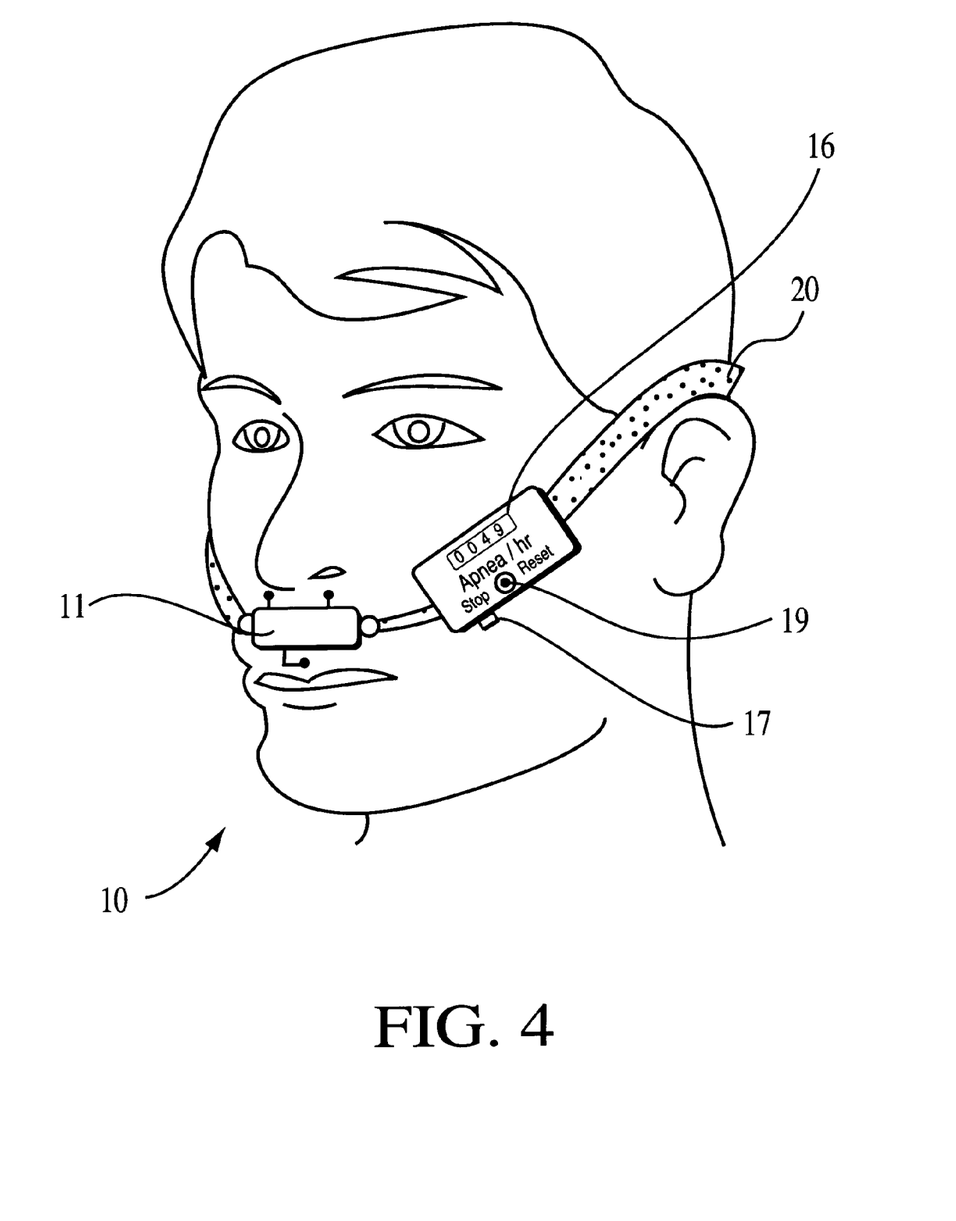
FIG. 4 is a diagram that shows the placement of an embodiment of the present invention on the head of a to-be-tested subject.

In another preferred embodiment, the present invention is seen to take the form of a non-tethered, apnea screening device 10. A general overview of this embodiment is shown in FIG. 3 which provides a schematic block diagram of the device. It is a battery operated device that comprises: (a) an airflow sensor 11 with appropriate signal conditioning and filtering circuitry 12 to yield required levels of signal fidelity, thus providing sensor output data that quantifies the temporal variations in the subject's upper respiratory airflow, (b) a programmable controller 13 with embedded programmable read only memory (PROM) to store control firmware including appropriate algorithms to identify, count and record the number of occurrences of specifically defined apnea events, while also compensating for drift in the amplitude of said sensor's airflow data, (c) memory 14 for storing time-stamped data, (d) an analog to digital converter 15 to sample sensor output data at prescribed time intervals, and (e) a data display means 16. FIG. 4 illustrates the placement of the present invention on a patient.

In another embodiment of the present invention, the non-tethered, apnea screening device further includes a mini jack 17 which allows connection to a smart cable for downloading the recorded data to an external computer system 18. This system has application software to analyze and display the temporal variations in the recorded data for the purpose of further evaluating the ambulatory subject for sleep apnea.

In another embodiment of the present invention, the non-tethered, apnea screening device further includes a control switch 19 that allows the display means 16 to recall and display the number of apnea events counted for each of the consecutive, specified periods of time that comprise the total period over which the airflow measurements were recorded, and to reset the controller 13 to begin again to count apnea events when the switch 19 remains depressed beyond a specified period of time, typically about five seconds.

Figure 5:
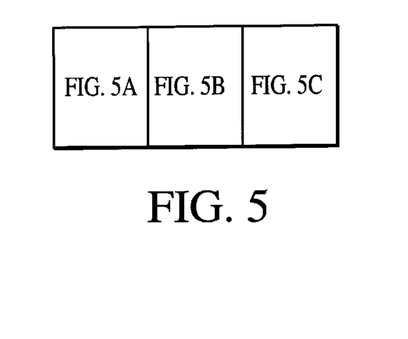
FIG. 5 is a schematic circuit diagram for the embodiment shown in FIG. 3.
Figure 5A:
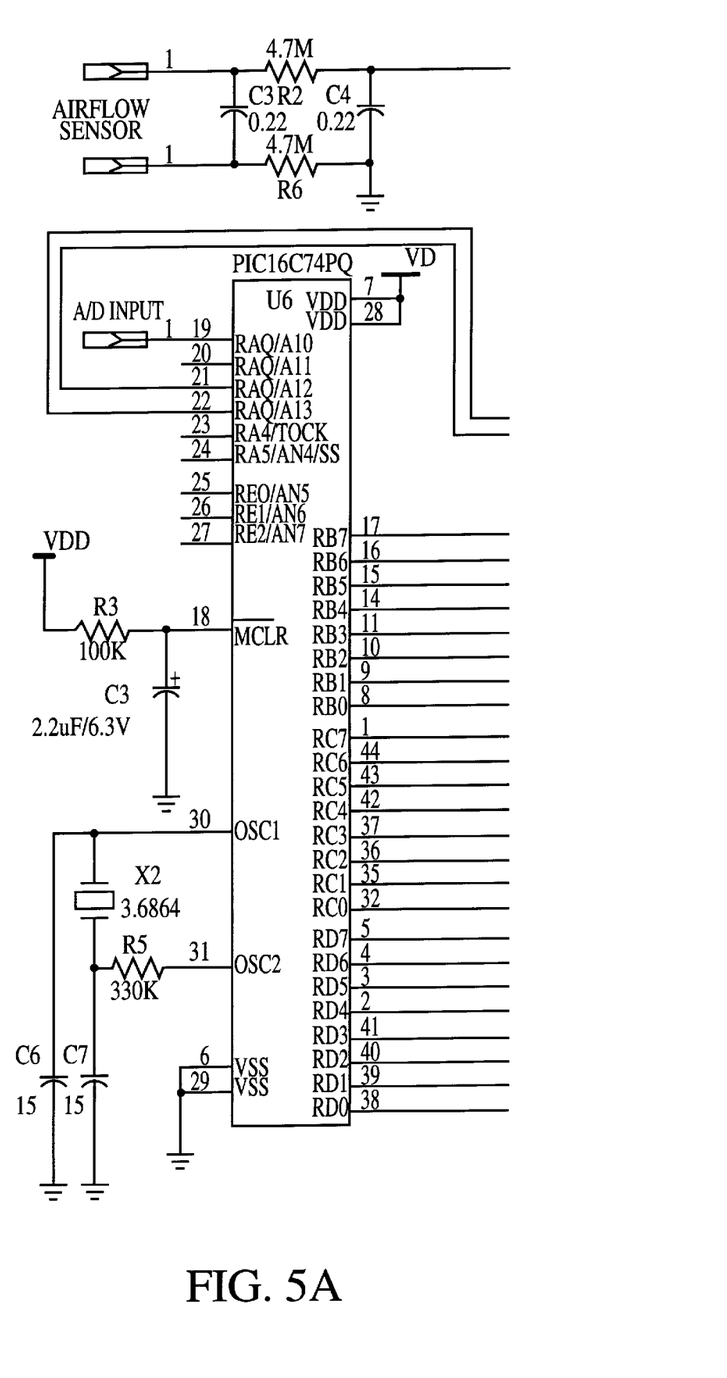
Figure 5B:
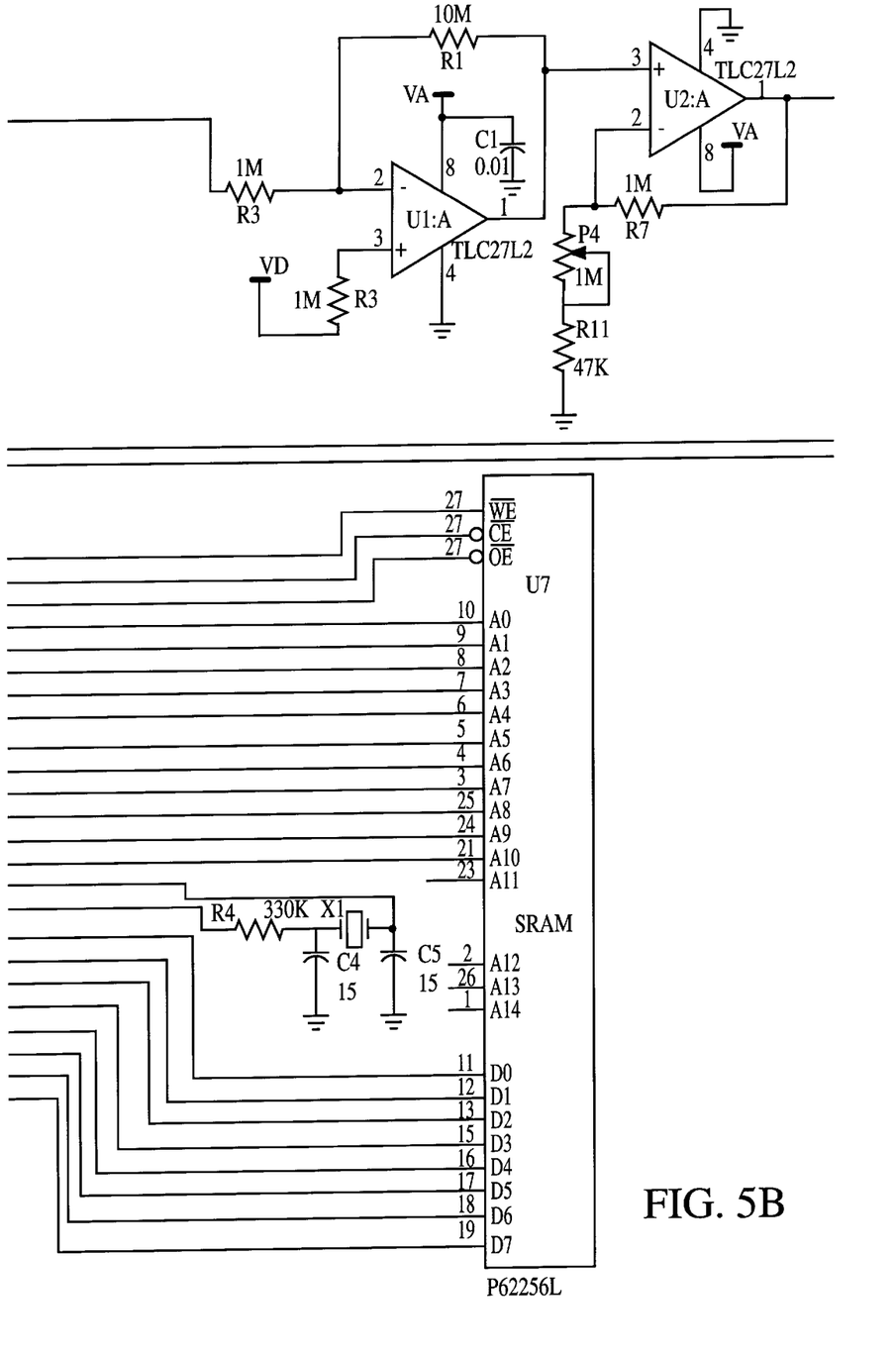
Figure 5C:
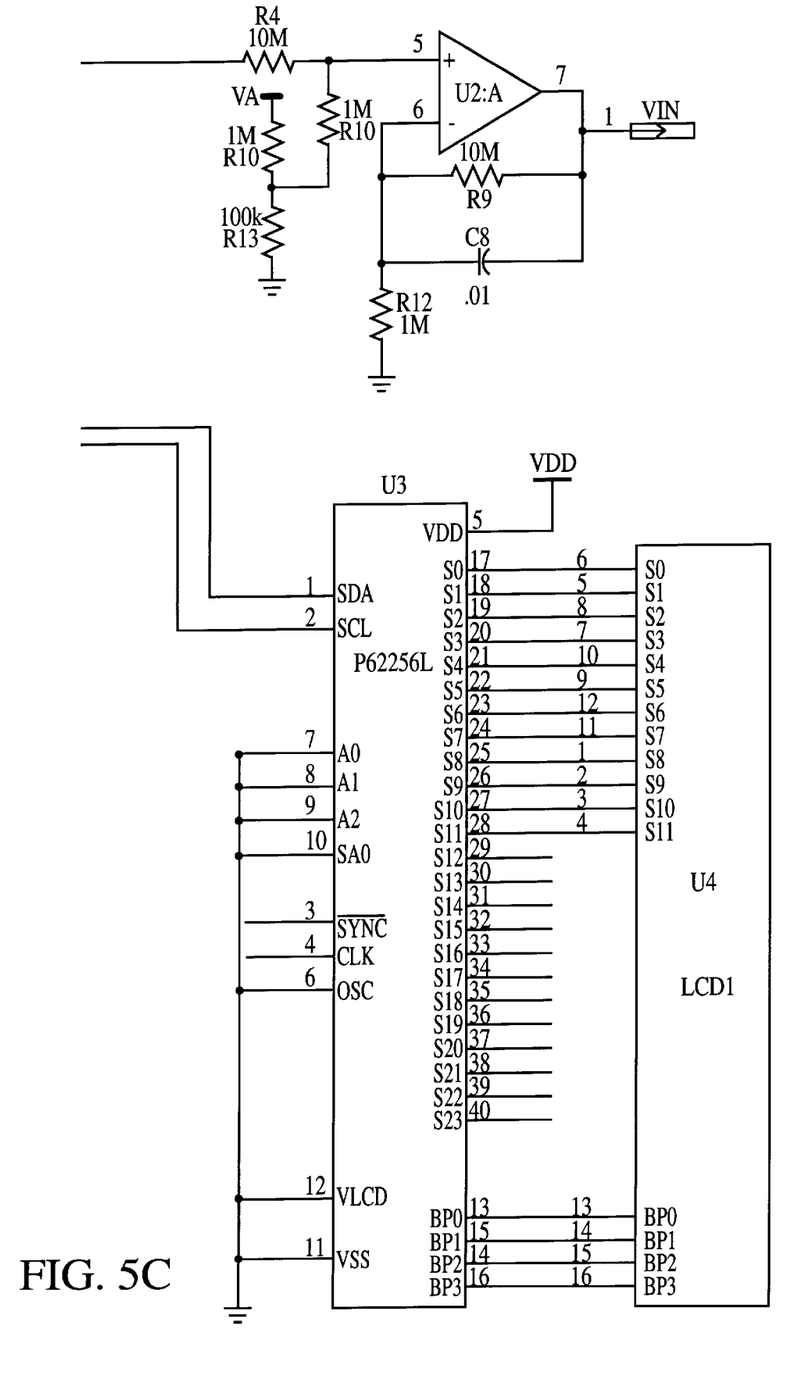

In a preferred embodiment of the present invention, the schematic circuit diagram for the device is illustrated in FIG. 5.

Appropriate hardware for use in this recorder unit includes: (a) an ultra-low power CMOS microprocessor controller (Microchip PIC16C74) for timing and system control, (b) programmable memory, (c) signal conditioning and filtering circuitry, (d) an 8 bit, analog to digital (A/D) converter for digitizing the analog signal, (e) 512K bytes or greater of SRAM, EEPROM or FLASH memory for storing the digitized signal, and (f) a LCD readout with a LCD driver chip. Support components and circuit chips are of surface mount technology (SMT).

This signal conditioning and filtering circuitry includes a high gain amplifier whose circuitry is adjusted to provide a band pass of about 0.15 to 0.80 hertz in order to measure the expected low frequency range of airflow associated with respiration, while filtering out the higher frequency ranges.

The 8 bit A/D converter of the present invention is set to sample the sensor output signal at ten data points per second. For these low frequency signals, this sampling rate yields good representation and detail for the sensor's analog signal. For a recording unit having 512K bytes of RAM storage and at this sampling frequency, there is fourteen hours of recording time. Standard digital sampling techniques are employed to record the airflow signal.

For monitoring the upper airway breathing of a subject, extensive bench tests were conducted on pressure, thermistor and thermocouple sensors.

Thermocouples were found to be very stable and repeatable while thermistor output and sensitivity output varied greatly from unit to unit. The advantage of thermocouples are that they are self generating (i.e., two dissimilar metals generate an output voltage when connected together at a junction), the output signal changes in proportion to inspired and expired air (cooling and heating) as it passes across the junction element. Thermocouples are very low impedance devices and exhibit more stable and predictable properties than do thermistors which tended to produce a static sensitive environment resulting from artifact distortion.

Combined nasal and oral airflow may be measured with a commercially-available, airflow sensor 11 of the thermocouple type, such a Pro-Tech cannula style, Model No. 1242, nasal/oral airflow sensor or the Rochester Electro-Medical No. 602640 sensor assembly. The Rochester unit is made of medical grade silicone tubing that is fully flexible to fit a variety of facial shapes. This design eliminates the need for taping, allows for simple easy adjustment and the soft tubing adds to patient comfort.

An adjustable elastic strap 20 is attached to the sensor assembly and worn around the back of the head for good stability and comfort. The strap also serves as a holding platform for attachment of the recorder unit which is attached at cheek level on one side of the face. Although the recorder unit may be a small, flat wafer (i.e., about 1.5× 1.9×0.4 inches, with soft rounded corners), frontal positioning of the unit was determined to be the most unobtrusive since attachment behind the head would be uncomfortable and might interfere with sleep. A short lead (i.e., 1–2 inches) between the sensor and the recorder unit is firmly attached to the strap (i.e., no tethered wires).

Pressure sensors provide another alternative means for making the necessary airflow measurement. For example, a standard oxygen nasal cannula, similar to a Sure Flow unit #33801 (B & F Medical), connected to a solid-state air pressure transducer, such as a Fuijikura type PSM-002KPG (Servoflo Corporation), can be substituted for the thermocouple (or thermistor) sensor to measure upper airway breathing. Air pressure has the advantage of producing a more stable signal even if the nasal cannula (soft plastic air tube) placed about the upper lip and near the nostrils is displaced or moves during sleep. The nares placed cannula is typically routed about the patient's ears, then under the chin and held in place by a lanyard style fastener. The cannula is then connected to a pressure transducer contained in the monitoring unit. This combination detects the pressure fluctuations caused by inspiration and expiration, with the signal's contour being basically proportional to the subject's airflow.

The device's recorder unit is uniquely configured to report apnea events (including both apneas and hypopneas) occurring per hour for apnea screening purposes. This recorder is outfitted with a visual readout and special firmware for counting apnea events.

This firmware employs an algorithm that finds the maximum and minimum signal levels in a preset time epoch (usually 5 seconds), effectively capturing the high and low points of a single breath with varying DC offsets. A potential apnea begins when a 'max-min" point falls below a specified threshold and ends when it rises above the same threshold.

The threshold is set in terms of a percentage, for example, 50%, of a "baseline amplitude" (DC level). This is the average "max-min" value determined at the start of the record.

To compensate for varying signal amplitudes as might be caused by minor displacements of the airflow sensor, an adaptive threshold algorithm is applied. This involves slowly adjusting the baseline amplitude throughout the recording while maintaining a fixed percentage of this baseline as the threshold. Means used to adjust this baseline include a 3 dB/octave low-pass filter with a time constant of typically three minutes. Alternatively, a more sophisticated adaptive threshold algorithm uses a "stack" (first in—first out list) which holds all the max-min points for an "adaptive period," typically a few minutes. For every time-step, a new max-min point is pushed onto the stack displaying the oldest. Then, periodically (typically every 10–15 seconds) the stack is sorted and the max-min value at a certain percentile (typically, the 80th) is taken to be the new adaptive baseline. From this, new percentage thresholds are derived.

The device's firmware was written in Assembly Language code using assembler software for the PIC Microchip. This program was initially burned into the electrically programmable/erasable read only memory (EPROM) in the PIC 16C74 microprocessor. After the program was finalized, a one-time programmable (OTP) memory PIC Microchip replaced the EPROM.

The smart cable for use with this recorder consists of a miniplug 17 at one end for connection to the recorder and a DB9 connector at the computer end. A very small SMT circuit board is contained within the DB9 shell and populated with an RS232 UART chip to establish data communications between the recorder and the computer. Power is taken from the computer's serial port. Application software manages the data transfer and formats the data into a convenient file structure.

Because of the signal fidelity achieved with the present invention, it is possible to use an external computer to further analyze the airflow data recorded using the present invention.

Although the foregoing disclosure relates to preferred embodiments of the invention, it is understood that these details have been given for the purposes of clarification only. Various changes and modifications of the invention will be apparent, to one having ordinary skill in the art, without departing from the spirit and scope of the invention as hereinafter set forth in the claims.

We claim:

1. A method for evaluating a fully ambulatory subject for sleep apnea, comprising the steps of:
   locating on the subject's upper lip an airflow sensor that is connected with a miniature, recording unit, said unit having signal conditioning and filtering circuitry to yield required levels of airflow sensor signal fidelity, a programmable controller with an analog to digital converter, an integrated recorder and a data display means, wherein said programmable controller having firmware that analyzes said signal,
   using said unit to sample at prescribed time intervals sensor data that quantifies the temporal variation of the subject's airflow,
   time stamping and storing said sampled data in said integrated recorder,
   using said firmware to identify, count and record in said integrated recorder the number of occurrences of specifically defined apnea events, and
   using said display means to visually communicate the number of apnea events identified by said firmware as occurring per a specified period of time.

2. A method for evaluating a fully ambulatory subject for sleep apnea, as recited in claim 1, wherein
   said controller having a control switch that allows said display means to recall and display the number of apnea events counted for each of the consecutive, specified periods of time that comprise the total period over which said airflow measurements were recorded, and to reset said controller to begin again to count apnea events when said switch remains depressed beyond a specified period of time.

3. A method for evaluating a fully ambulatory subject for sleep apnea, as recited in claim 1, further comprising the steps:
   providing said unit with a mini jack that connects with a smart cable to control data flow between said recorder and an external computer, and
   using said external computer with application software to analyze and display the temporal variations in said data for the purpose of evaluating the ambulatory subject for sleep apnea.

4. A method for evaluating a fully ambulatory subject for sleep apnea, as recited in claim 2, further comprising the steps:
   providing said unit with a mini jack that connects with a smart cable to control data flow between said recorder and an external computer, and
   using said external computer with application software to analyze and display the temporal variations in said data for the purpose of evaluating the ambulatory subject for sleep apnea.

5. A method for evaluating a fully ambulatory subject for sleep apnea, as recited in claim 1, wherein:
   said firmware having an algorithm that finds the maximum and minimum signal levels in a preset time epoch, computes the difference between said signal levels and defines an apnea event as occurring when said signal level difference falls below and stays below a specified threshold for a prescribed period of time,
   said threshold being set in terms of a percentage of the average over a specified number of time epochs of the difference between said signal levels.

6. A method for evaluating a fully ambulatory subject for sleep apnea, as recited in claim 4, wherein:
   said firmware having an algorithm that finds the maximum and minimum signal levels in a preset time epoch, computes the difference between said signal levels and defines an apnea event as occurring when said signal level difference falls below and stays below a specified threshold for a prescribed period of time,
   said threshold being set in terms of a percentage of the average over a specified number of time epochs of the difference between said signal levels.

7. A device for evaluating a fully ambulatory subject for sleep apnea, said device comprising:
   an airflow sensor located so as to measure the subject's airflow,
   a miniature, recording unit connected to said sensor, said unit having signal conditioning and filtering circuitry to yield required levels of signal fidelity, a programmable controller connected to said sensor and circuitry, said controller connected to and controlling both an analog to digital converter and an integrated recorder, and a data display means connected to said controller, wherein said programmable controller having firmware that analyzes said signal to identify, count, record in said integrated recorder, and display in said display means the number of occurrences of specifically defined apnea events.

8. A device for evaluating a fully ambulatory subject for sleep apnea, as recited in claim 7, said device further comprising:

a control switch connected to said controller that allows said display means to recall and display the number of apnea events counted for each of the consecutive, specified periods of time that comprise the total period over which said airflow measurements were recorded, and to reset said controller to begin again to count apnea events when said switch remains depressed beyond a specified period of time.

9. A device for evaluating a fully ambulatory subject for sleep apnea, as recited in claim 7, said device further comprising:

a mini jack connected to said recorder, wherein said jack connects with an external smart cable to control data flow between said recorder and an external computer, wherein said external computer having application software to analyze and display the temporal variations in said data for the purpose of evaluating the ambulatory subject for sleep apnea.

10. A device for evaluating a fully ambulatory subject for sleep apnea, as recited in claim 7, said device further comprising:

a mini jack connected to said recorder, a smart cable that connects with said mini jack to control data flow between said recorder and an external computer, wherein said external computer having application software to analyze and display the temporal variations in said data for the purpose of evaluating the ambulatory subject for sleep apnea.

11. A device for evaluating a fully ambulatory subject for sleep apnea, as recited in claim 7, wherein:

said firmware having an algorithm that finds the maximum and minimum signal levels in a preset time epoch, computes the difference between said signal levels and defines an apnea event as occurring when said signal level difference falls below and stays below a specified threshold for a prescribed period of time, said threshold being set in terms of a percentage of the average over a specified number of time epochs of the difference between said signal levels.

12. A device for evaluating a fully ambulatory subject for sleep apnea, as recited in claim 8, wherein:

said firmware having an algorithm that finds the maximum and minimum signal levels in a preset time epoch, computes the difference between said signal levels and defines an apnea event as occurring when said signal level difference falls below and stays below a specified threshold for a prescribed period of time, said threshold being set in terms of a percentage of the average over a specified number of time epochs of the difference between said signal levels.

13. A device for evaluating a fully ambulatory subject for sleep apnea, as recited in claim 9, wherein:

said firmware having an algorithm that finds the maximum and minimum signal levels in a preset time epoch, computes the difference between said signal levels and defines an apnea event as occurring when said signal level difference falls below and stays below a specified threshold for a prescribed period of time, said threshold being set in terms of a percentage of the average over a specified number of time epochs of the difference between said signal levels.

14. A device for evaluating a fully ambulatory subject for sleep apnea, as recited in claim 10, wherein:

said firmware having an algorithm that finds the maximum and minimum signal levels in a preset time epoch, computes the difference between said signal levels and defines an apnea event as occurring when said signal level difference falls below and stays below a specified threshold for a prescribed period of time, said threshold being set in terms of a percentage of the average over a specified number of time epochs of the difference between said signal levels.

15. A device for evaluating a fully ambulatory subject for sleep apnea, said device comprising:

an airflow sensor located so as to measure the subject's airflow, a miniature, recording unit integrated with said sensor, said unit having signal conditioning and filtering circuitry to yield required levels of signal fidelity, a programmable controller connected to said sensor and circuitry, said controller connected to and controlling both an analog to digital converter and an integrated recorder, and a data display means connected to said controller, wherein said programmable controller having firmware that analyzes said signal to identify, count, and display in said display means the number of occurrences of specifically defined apnea events.

16. A device for evaluating a fully ambulatory subject for sleep apnea, as recited in claim 15, said device further comprising:

a control switch connected to said controller that allows said display means to recall and display the number of apnea events counted for each of the consecutive, specified periods of time that comprise the total period over which said airflow measurements were recorded, and to reset said controller to begin again to count apnea events when said switch remains depressed beyond a specified period of time.

17. A device for evaluating a fully ambulatory subject for sleep apnea, as recited in claim 15, said device further comprising:

a mini jack connected to said recorder, wherein said jack connects with an external smart cable to control data flow between said recorder and an external computer, wherein said external computer having application software to analyze and display the temporal variations in said data for the purpose of evaluating the ambulatory subject for sleep apnea.

18. A device for evaluating a fully ambulatory subject for sleep apnea, as recited in claim 15, said device further comprising:

a mini jack connected to said recorder, a smart cable that connects with said mini jack to control data flow between said recorder and an external computer, wherein said external computer having application software to analyze and display the temporal variations in said data for the purpose of evaluating the ambulatory subject for sleep apnea.

19. A device for evaluating a fully ambulatory subject for sleep apnea, as recited in claim 15, wherein:

said firmware having an algorithm that finds the maximum and minimum signal levels in a preset time epoch, computes the difference between said signal levels and defines an apnea event as occurring when said signal level difference falls below and stays below a specified threshold for a prescribed period of time, said threshold being set in terms of a percentage of the average over a specified number of time epochs of the difference between said signal levels.

20. A device for evaluating a fully ambulatory subject for sleep apnea, as recited in claim 17, wherein:

said firmware having an algorithm that finds the maximum and minimum signal levels in a preset time epoch, computes the difference between said signal levels and defines an apnea event as occurring when said signal level difference falls below and stays below a specified threshold for a prescribed period of time, said threshold being set in terms of a percentage of the average over a specified number of time epochs of the difference between said signal levels.

* * * * *